(12) United States Patent
Dasbach

(10) Patent No.: US 11,103,648 B2
(45) Date of Patent: Aug. 31, 2021

(54) INJECTOR ASSEMBLY

(71) Applicant: SANOFI-AVENTIS DEUTSCHLAND GMBH, Frankfurt am Main (DE)

(72) Inventor: Uwe Dasbach, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 385 days.

(21) Appl. No.: 16/300,420

(22) PCT Filed: May 5, 2017

(86) PCT No.: PCT/EP2017/060786
§ 371 (c)(1),
(2) Date: Nov. 9, 2018

(87) PCT Pub. No.: WO2017/191305
PCT Pub. Date: Nov. 9, 2017

(65) Prior Publication Data
US 2020/0345949 A1   Nov. 5, 2020

(30) Foreign Application Priority Data

May 6, 2016  (EP) ..................................... 16168538

(51) Int. Cl.
*A61M 5/32* (2006.01)
*A61M 5/24* (2006.01)

(52) U.S. Cl.
CPC ........ *A61M 5/3202* (2013.01); *A61M 5/3204* (2013.01); *A61M 5/3271* (2013.01);
(Continued)

(58) Field of Classification Search
CPC .............. A61M 5/3202; A61M 5/3204; A61M 5/3271; A61M 2005/2474; A61M 5/24; A61M 5/3272
See application file for complete search history.

(56) References Cited

U.S. PATENT DOCUMENTS 5,242,401 A * 9/1993 Colsky .................. A61M 5/326
604/110
5,843,036 A * 12/1998 Olive .................. A61M 5/2033
604/136
(Continued)

FOREIGN PATENT DOCUMENTS

CN     101166551     4/2008
CN     102458531     5/2012
(Continued)

OTHER PUBLICATIONS

International Preliminary Report on Patentability in Application No. PCT/EP2017/060786, dated Nov. 6, 2018, 6 pages.
(Continued)

*Primary Examiner* — Bradley J Osinski
(74) *Attorney, Agent, or Firm* — Fish & Richardson P.C.

(57) ABSTRACT

An injector for delivering a liquid medicament is provided. The injector comprises: a housing having an opening at a first end and a cartridge contained within the housing, wherein the cartridge comprises a first fitting mechanism which is directed outwards from the opening of the housing; a removable cap; and a needle assembly supported on the removable cap, wherein the needle assembly has a second fitting mechanism which is directed outwards from a distal end of the removable cap, the removable cap being further configured such that each of the distal end and the proximal end of the removable cap are engageable with the opening of the housing, wherein the first fitting mechanism is complementary with the second fitting mechanism such that the needle assembly is connectable to the cartridge by joining the first and second fitting mechanisms.

14 Claims, 9 Drawing Sheets

(52) U.S. Cl.
CPC ............. *A61M 5/24* (2013.01); *A61M 5/3272* (2013.01); *A61M 2005/2474* (2013.01)

(56) References Cited

U.S. PATENT DOCUMENTS

| | | | |
|---|---|---|---|
| 8,287,492 B2* | 10/2012 | Schraga | A61M 5/329 604/110 |
| 2006/0270984 A1* | 11/2006 | Hommann | A61M 5/3202 604/134 |
| 2011/0137247 A1 | 6/2011 | Mesa et al. | |
| 2014/0213985 A1 | 7/2014 | Teucher et al. | |
| 2015/0367072 A1 | 12/2015 | Constantineau et al. | |

FOREIGN PATENT DOCUMENTS

| | | |
|---|---|---|
| CN | 102802704 | 11/2012 |
| CN | 104379196 | 2/2015 |
| CN | 104436369 | 3/2015 |
| CN | 104436373 | 3/2015 |
| DE | 102004001811 | 8/2005 |
| EP | 2420271 | 2/2012 |
| WO | WO 2006017732 | 2/2006 |
| WO | WO 2010139666 | 12/2010 |
| WO | WO 2010142813 | 12/2010 |
| WO | WO 2012020089 | 2/2012 |
| WO | WO 2014001319 | 1/2014 |
| WO | WO 2014139912 | 9/2014 |

OTHER PUBLICATIONS

International Search Report and Written Opinion in Application No. PCT/EP2017/060786, dated Aug. 16, 2017, 8 pages.

* cited by examiner

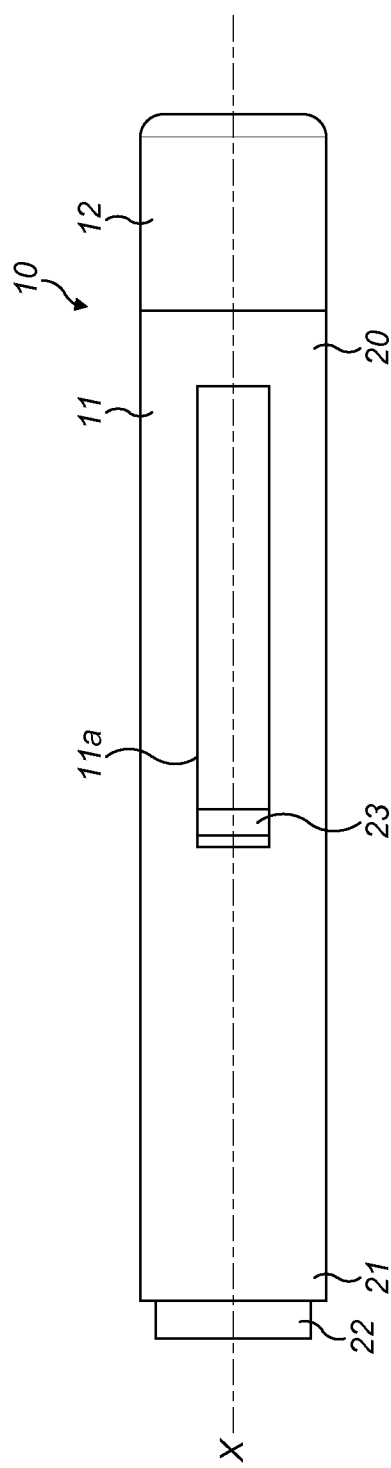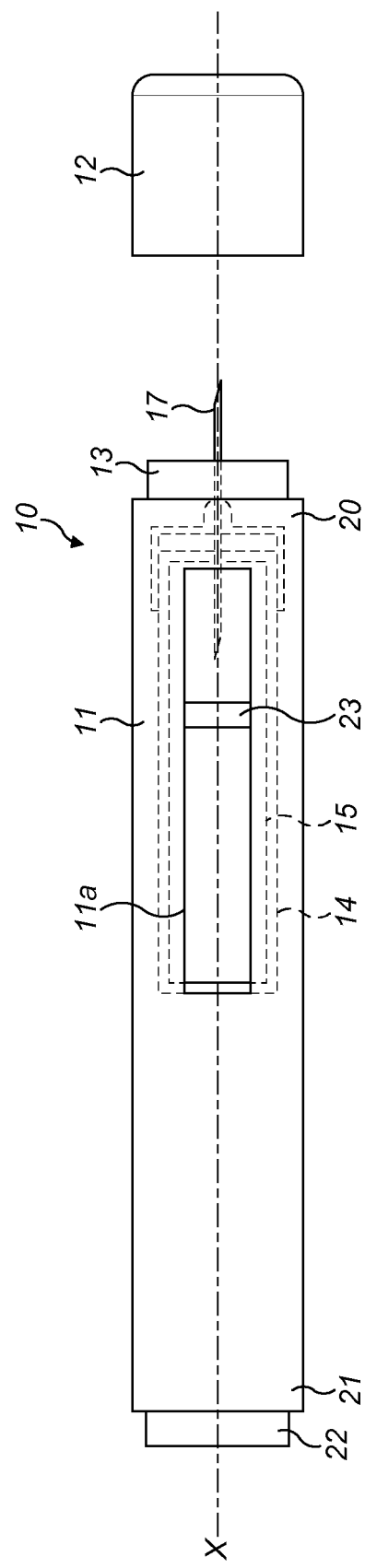

INJECTOR ASSEMBLY

CROSS REFERENCE TO RELATED APPLICATIONS

The present application is a national stage entry of International Patent Application No. PCT/EP2017/060786, filed on May 5, 2017, and claims priority to European Patent Application No. 16168538.3, filed on May 6, 2016, the entire contents of each of which are incorporated herein by reference.

TECHNICAL FIELD

The present disclosure relates to an injector assembly.

BACKGROUND

Current therapies delivered by means of self-administered injections include drugs for diabetes (both insulin and new GLP-A class drugs), migraine, hormone therapies, anticoagulants etc. Administering an injection is a process which presents a number of risks and challenges for user and healthcare professionals, both mental and physical.

Conventional injection devices typically fall under two categories—manual devices and auto-injectors. In a conventional manual device, a user must provide a force to drive a liquid medicament out of the device, e.g. by depressing a plunger.

Auto-injectors aim to make self-administration of injected therapies easier for users. Auto-injectors are devices which completely or partially replace activities involved in medicament delivery of manual devices. These activities may include removal of a protective syringe cap, insertion of a needle into a patient's skin, injection of the medicament, removal of the needle, shield of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth.

Some of the manual devices and auto-injectors operate with a cartridge-based injection system. This type of system is typically provided with a separate cartridge pre-filled with medicament and a separate needle sealed in a sterilized packaging. Before injection, the user has to place the cartridge in a cartridge holder located within the housing of the device, unseal the packaging containing the needle, and position the needle in the housing of the device. This may be considered time-consuming by some users.

Some other manual devices and auto-injectors include pre-filled cartridges that are often stored for a relatively long time before being effectively used for injection. One problem is that, during this time of storage, the medicament remains in contact with the needle of the cartridge and a clogging of the needle by the medicament may occur. This may delay the delivery of medicament during the injection and therefore increase the injection time.

SUMMARY

According to an aspect, there is provided an injector for delivering a liquid medicament, comprising: a housing having an opening at a first end and a cartridge contained within the housing, wherein the cartridge comprises a first fitting mechanism which is directed outwards from the opening of the housing; a removable cap; and a needle assembly supported on the removable cap, wherein the needle assembly has a second fitting mechanism which is directed outwards from a distal end of the removable cap, the removable cap being further configured such that each of the distal end and the proximal end of the removable cap are engageable with the opening of the housing, wherein the first fitting mechanism is complementary with the second fitting mechanism such that the needle assembly is connectable to the cartridge by joining the first and second fitting mechanisms.

The first and second fitting mechanisms may form a snap-fit arrangement or a screw-fit arrangement. The snap-fit arrangement allows the needle assembly and the cartridge to be connected quickly and easily. The screw-fit arrangement allows the needle assembly and the cartridge to be connected securely.

The distal end and the proximal end of the removable cap may both be cylindrical shaped and have a diameter same as a diameter of the opening of the housing, such that the distal end and the proximal can be alternatively accommodated into the opening of the housing.

The distal end and the proximal end of the removable cap may each comprise a rim having an inner diameter that is the same as a diameter of the opening of the housing, such that opening of the housing can be accommodated into the distal end and the proximal end of the removable cap alternatively.

The needle assembly may comprise a hollow needle which opens towards a proximal end of the removable cap, and a needle shield arranged to cover the hollow needle. The needle shield acts to cover the needle before injection so as to prevent damage to the needle.

The needle shield may be fixedly attached to the removable cap such that it can be removed together with the removable cap once the needle assembly is connected to the cartridge.

The injector may further comprise a needle holder arranged at the first end of the cartridge, wherein when the needle assembly is connected to the cartridge, the needle is arranged to pierce through the needle holder such that the needle holder operationally positions the needle. The needle holder ensures that the needle is appropriately held in place during injection so as to prevent problems associated with the dispensing of the liquid medicament.

The cartridge may be arranged to be slidable along the length of the housing towards the opening, when the removable cap is removed from the injector.

The injector may further comprise a guide pin arranged on an inner surface of the housing, a retractable sleeve arranged at the first end of the housing, and a spring element arranged on the inner surface of the housing so as to bias the retractable sleeve outwards from the opening of the housing, wherein the retractable sleeve comprises a guide path, and the guide pin is arranged to be moveable along the guide path so as to control the extension and retraction of the retractable sleeve.

The retractable sleeve may comprise a first part and a second part, wherein the first part is arranged to contact an injection site, and the second part is arranged to move axially together with the first part and to rotate with respect to the first part, further wherein the guide path is arranged at the second part of the retractable sleeve.

The retractable sleeve may be biased by a spring element towards the proximal end of the housing and outwards from the opening of the housing.

The guide path may comprise a first end portion, a first bend, a second bend, a third bend, and a second end portion, wherein the first end portion, the first bend, the second bend, the third bend, and the second end portion form a zigzag shape.

The guide path may further comprise an elastic arm arranged at the second end portion of the of the guide path, the elastic arm being arranged to lock the guide pin in place when the guide pin reaches the second end portion in the guide path.

The removable cap may further comprise a removable seal arranged to cover the distal end.

The injector may contain medicament.

These and other aspects will be apparent from and elucidated with reference to the embodiments described hereinafter.

BRIEF DESCRIPTION OF THE DRAWINGS

Various embodiments will now be described, by way of example only, with reference to the accompanying drawings, in which:

FIGS. 1A and 1B are side-on views of an example of an auto-injector device according to an embodiment;

Reference will now be made in detail to the embodiments of the present disclosure, examples of which are illustrated in the accompanying drawings, wherein like reference numerals refer to like elements throughout.

DETAILED DESCRIPTION

Figure 2:
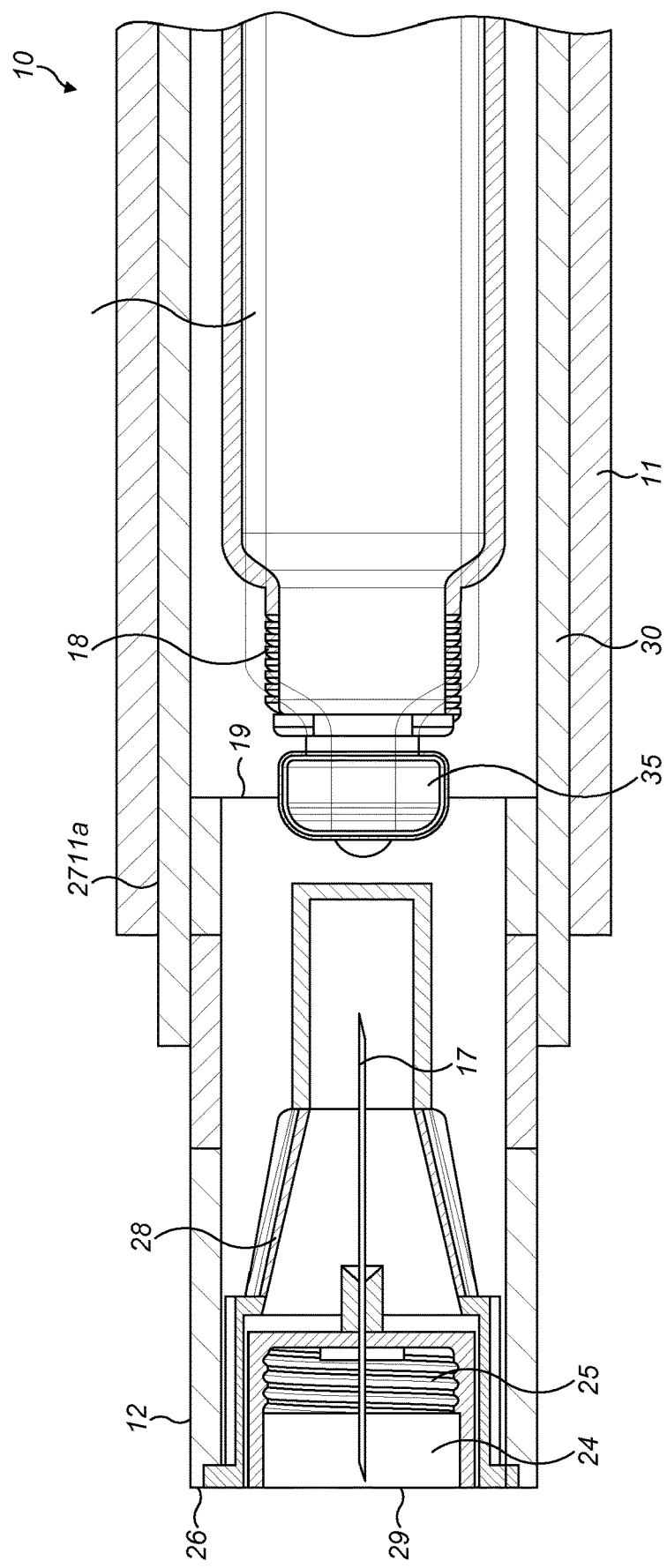
FIG. 2 is a cross-sectional view of an example of an injector device in a first state, according to an embodiment.

An injector assembly suitable for manual injection devices and auto-injector devices is provided. The injector assembly includes a body containing a cartridge, and a removable cap. The cartridge includes a hollow body which holds a liquid medicament, a first fitting mechanism, and a needle holder. The removable cap includes a needle assembly. The needle assembly includes a hollow injection needle and a second fitting mechanism.

In an initial configuration of the injector assembly, a distal end of the removable cap is engaged with the body of the injector, such that the hollow injection needle is not connected to the cartridge. A user can disengage the removable cap and engage a proximal end of the cap to the housing, such that the first fitting mechanism and second fitting mechanism connect together. The hollow injection needle of the needle assembly engages with the needle holder such that when the removable cap is removed again from the body, the needle is operationally positioned for injection.

Since the injection needle is not engaged with the syringe until before an injection when the user disengages the proximal end of the cap from the body and attaches the distal end to the body, the injector assembly can reduce problems associated with clogging of the injection needle. The injector assembly can also reduce the risk of stick injury because the user does not have to directly handle the injection needle when assembling the injector device. Furthermore, preparing the injection device for use can be relatively simple. For example, in some implementations, instead of needing to handle three separate components (the main body, the needle assembly and the cap), only two components need to be handled. The resulting simplified use may allow the injection device to be used by a greater proportion of the population.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

FIG. 2 is a cross-sectional view of an injector device in a first state, according to a first embodiment.

FIG. 2 shows an injector device 10 comprising a housing 11, and a removable cap 12. The housing 11 has an opening at a first end. A cartridge 11a is contained within the housing 11 and a needle holder 35 is arranged at a proximal end of the housing, i.e. the direction pointing towards the patient during an injection. The cartridge 11a is arranged to contain liquid medicament that is to be dispensed to a user during injection.

A retractable sleeve 30 is arranged on an inner surface of the housing 11. The retractable sleeve 30 is a cylindrical sleeve arranged near the proximal end of the injector device 10, and is arranged such that it can protrude from the opening 19 of the housing 11 and be retracted into the housing 11. The retractable sleeve 30 is biased to protrude outwards from the proximal end of the housing 11 by a spring element (not shown in the drawings). In the first state, the retractable sleeve 30 is retained within the housing 11, against the spring force provided by the spring element, due to the presence of the removable cap 12 which is in the first state attached to the housing 11.

Moreover, in the present embodiment, the retractable sleeve 30 comprises a guide path (not shown in FIGS. 2 to 6) at which a guide pin (not shown in FIGS. 2 to 6) arranged on an inner surface of housing 11 can be engaged such that the guide pin is movable along the guide path. Details of the operation of the retractable sleeve 30, the guide path, and the guide pin will be explained with respect to FIGS. 7 to 11.

The housing 11 comprises an opening 19 for engaging with the removable cap 12. Specifically, the opening 19 of the housing 11 is configured and/or shaped such that each of a distal end 26 and a proximal end 27 of the removable cap are engageable with the opening of the housing. In the present embodiment, the opening 19 is a round aperture defined by the cylindrical wall of the housing 11 having a diameter D1, while both the distal end 26 and the proximal end 27 of the removable cap 12 are also cylindrical shaped having a diameter D2, where D2=D1. Hence, both the distal end 26 and the proximal end 27 of the removable cap 12 can be accommodated in a snug fit into the round aperture at the opening 19 alternatively. In a first state, i.e. before use, the proximal end 27 of the removable cap is engaged with the opening 19 of the housing. This is illustrated in FIG. 2.

The cartridge comprises a first fitting mechanism 18 which is directed outwards from the opening of the housing 11. In this particular embodiment, the first fitting mechanism 18 is a threaded arrangement on an outer surface at the end of the cartridge 11a.

The needle holder 35 is used to operationally position the hollow injection needle 17 when the needle assembly 24 initially contained in the removable cap 12 is connected with the cartridge 11a contained in the housing 11. The needle holder 35 in the present embodiment is substantially cylindrical shaped such that it can be accommodated in a snug fit into the needle assembly 24 when the needle assembly 24 is connected to the cartridge 11a contained in the housing 11.

As shown in FIG. 2, a needle assembly 24 is supported on the removable cap 12. In this embodiment, the needle assembly 24 is supported on the removable cap by means of an elastic clip element (not shown in the drawing) which releasably holds the needle assembly in place on the removable cap 12. The needle assembly 24 comprises a second fitting mechanism 25 and a hollow injection needle 17 that is covered by a needle shield 28. As described above, the removable cap 12 comprises a distal end 26, i.e. pointing away from the injection site of the patient during injection, and a proximal end 27, i.e. pointing towards the injection site of the patient during injection. The second fitting mechanism 25 is directed outwards from the distal end 26 of the removable cap 12.

The second fitting mechanism 25 of the needle assembly 24 is arranged near the distal end 26 of the removable cap 12, such that in the first state, i.e. before use, the second fitting mechanism 25 is located away from the first fitting mechanism 18 in the housing 11. In this particular embodiment, the second fitting mechanism 25 is a threaded arrangement on an inner surface of the needle assembly 24, near the distal end 26 of the removable cap 12. In other words, the first fitting mechanism 18 and the second fitting mechanism 25 form a screw-fit arrangement.

The needle shield 28 in the present embodiment is fixedly attached to the removable cap 12 such that it is removable together with the removable cap 12, once the needle assembly 24 is connected to the cartridge 11a. In other words, when the removable cap 12 is removed from the housing 11 in the first state, the needle shield 28 remains supported on the removable cap 12. Also, after the distal end 26 of the removable cap 12 is engaged with the opening 19 of the housing 11 and the first fitting mechanism 18 connects with the second fitting mechanism 25, the removable cap 12 can be removed again together with the needle shield 28, so as to expose the hollow injection needle 17 ready for injection.

A removable seal 29 is arranged at the distal end 26 of the removable cap 12. Hence, when the injector device 10 is in the first state (i.e. before use) where the proximal end 27 of the removable cap 12 is engaged with the opening 19 of the housing 11, the needle assembly 24 including the hollow injection needle 17 and the second fitting mechanism 25 are kept in a sterile environment in order to prevent contamination (e.g. microbial contamination), before the second fitting mechanism 25 is connected with the first fitting mechanism 18 in the housing 11. The removable seal 29 is made of a plastic film or a film comprising plastic and metal layers, for instance.

The removable seal 29 is arranged to be removed from the removable cap 12 after the removable cap 12 is disengaged from the housing 11 from its first state (i.e. when the proximal end 27 of the removable cap 12 being engaged with the opening 19 of the housing 11), and before the distal end 26 of the removable cap 12 is engaged with the opening 19 of the housing 11. Once the seal 29 has been removed, the second fitting mechanism 25 of the removable cap 12 can be connected with the first fitting mechanism at the cartridge 11a contained within the housing 11, by engaging the distal end 26 of the removable cap 12 with the opening 19 of the housing 11.

The cartridge 11a contained in the housing 11 is arranged to be slidable. When the removable cap 12 is temporarily removed from the housing 11 from the initial state, the cartridge 11a can be translated along the length of the housing 11 towards the opening 19. Therefore, the cartridge 11a protrudes from the opening 19 of the housing 11 such that it is ready to engage with the second fitting mechanism 25 at the removable cap 12. This will be described in further detail with respect to FIG. 3. The sliding movement of the cartridge 11a may be manually controlled via a sliding mechanism provided at the housing 11 of the injector device 10.

Figure 3:
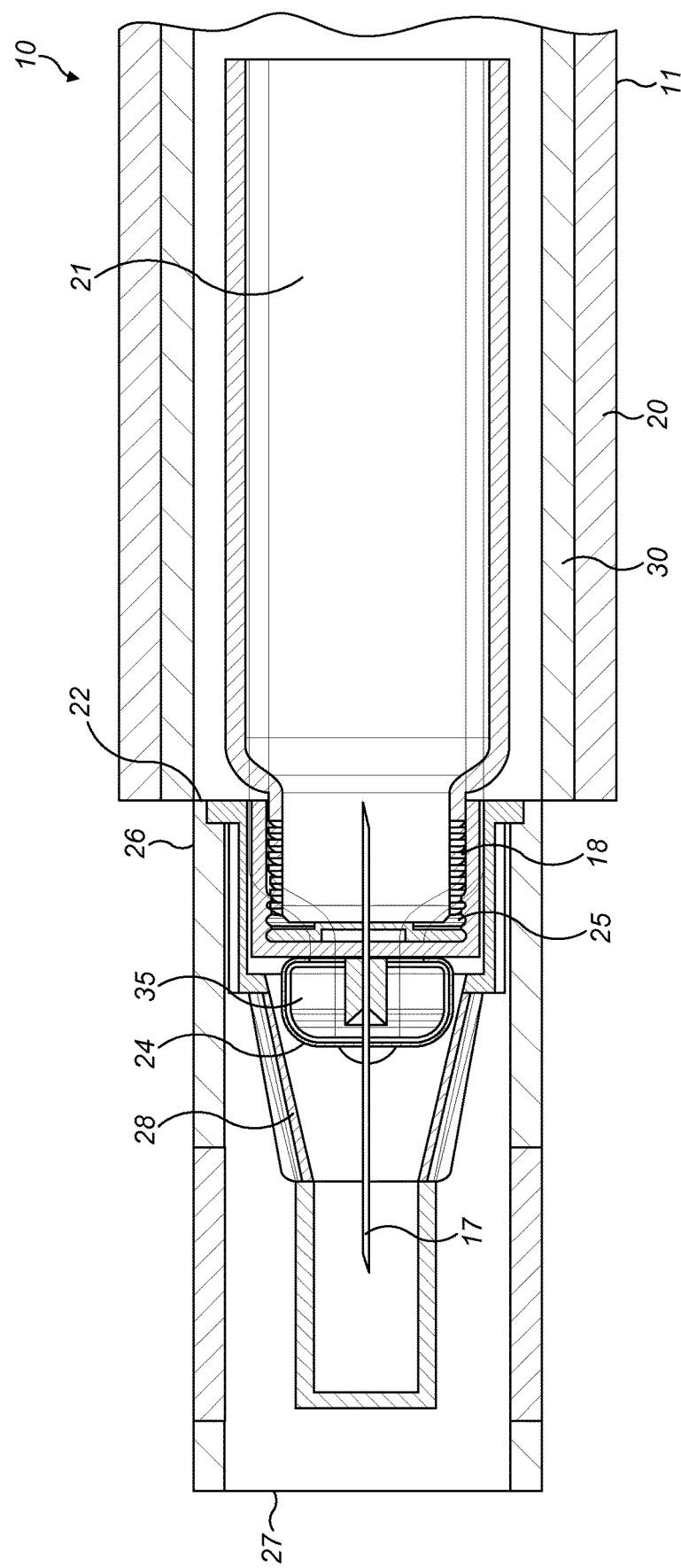
FIG. 3 is a cross-sectional view of the injector device of FIG. 2 in a second state.

FIG. 3 is a cross-sectional view of the injector device of FIG. 2 in a second state.

As described with respect to FIG. 2 in the above, from the first state the proximal end 27 of the removable cap 12 is disengaged from the opening 19 of the housing 11 when the removable cap 12 is removed from the housing 11. The cartridge 11a contained in the housing 11 is then translated towards the opening 19 of the housing such that it protrudes from the opening 19, such that the first fitting mechanism 18 is ready to join with the second fitting mechanism 25 at the removable cap 12.

The removable seal 29 which initially covers the distal end 26 of the removable cap 12 is then removed, so as to expose an end of the hollow injection needle 17 and the second fitting mechanism 25 for engaging with the first fitting mechanism 18 at the cartridge 11a.

The removable cap 12 is then reversed and the distal end 26 of the removable cap 12 is engaged with the opening 19 of the housing 11. Specifically, in the present embodiment, the threaded outer surface of the first fitting mechanism 18 receives and engages with the threaded inner surface of the second fitting mechanism 25 in the needle assembly 24 supported on the removable cap 12.

At the same time, the end of the hollow injection needle 17 engages with the needle holder 35 and pierces through a center of the needle holder, such that the needle holder 35 operationally positions the hollow injection needle 17 for injection.

Figure 4:
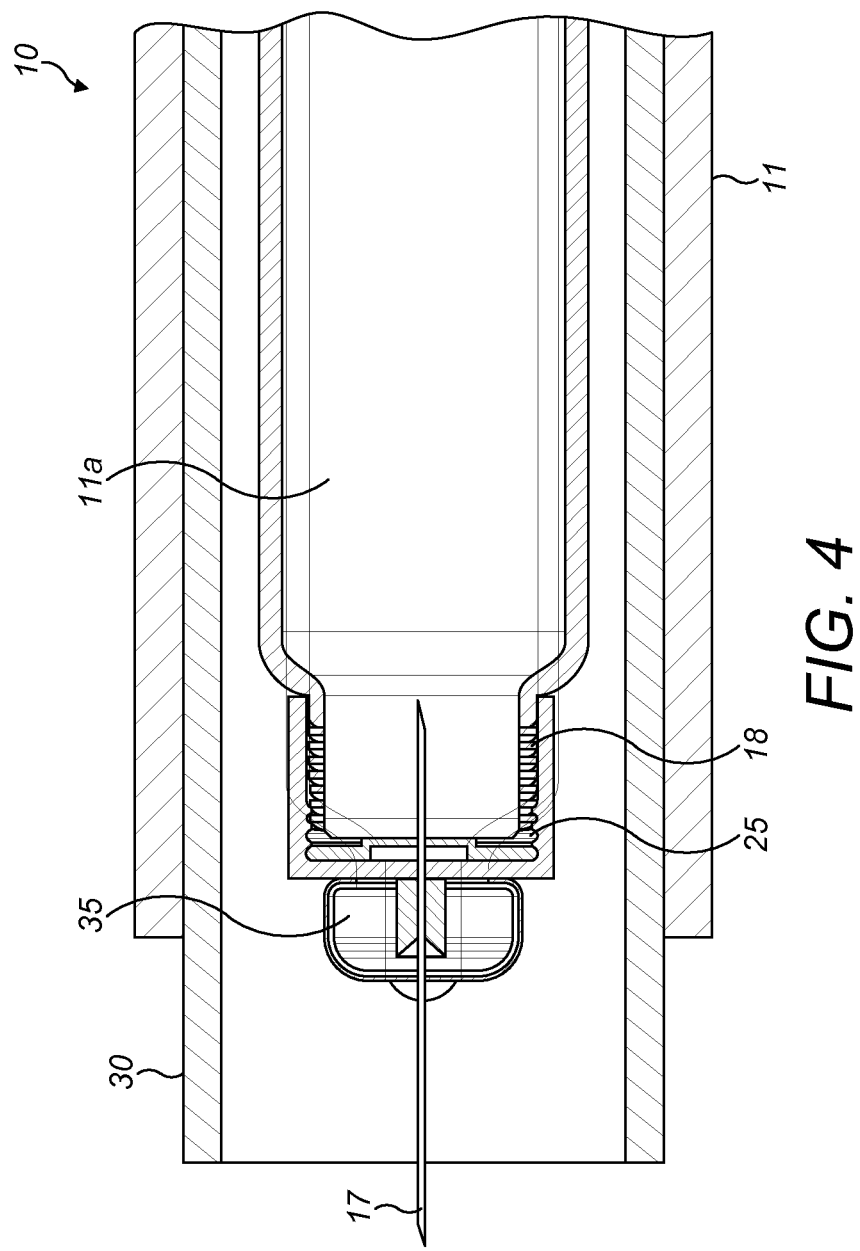
FIG. 4 is a cross-sectional view of the injector device of FIGS. 2 and 3 in a third state.
Figure 5:
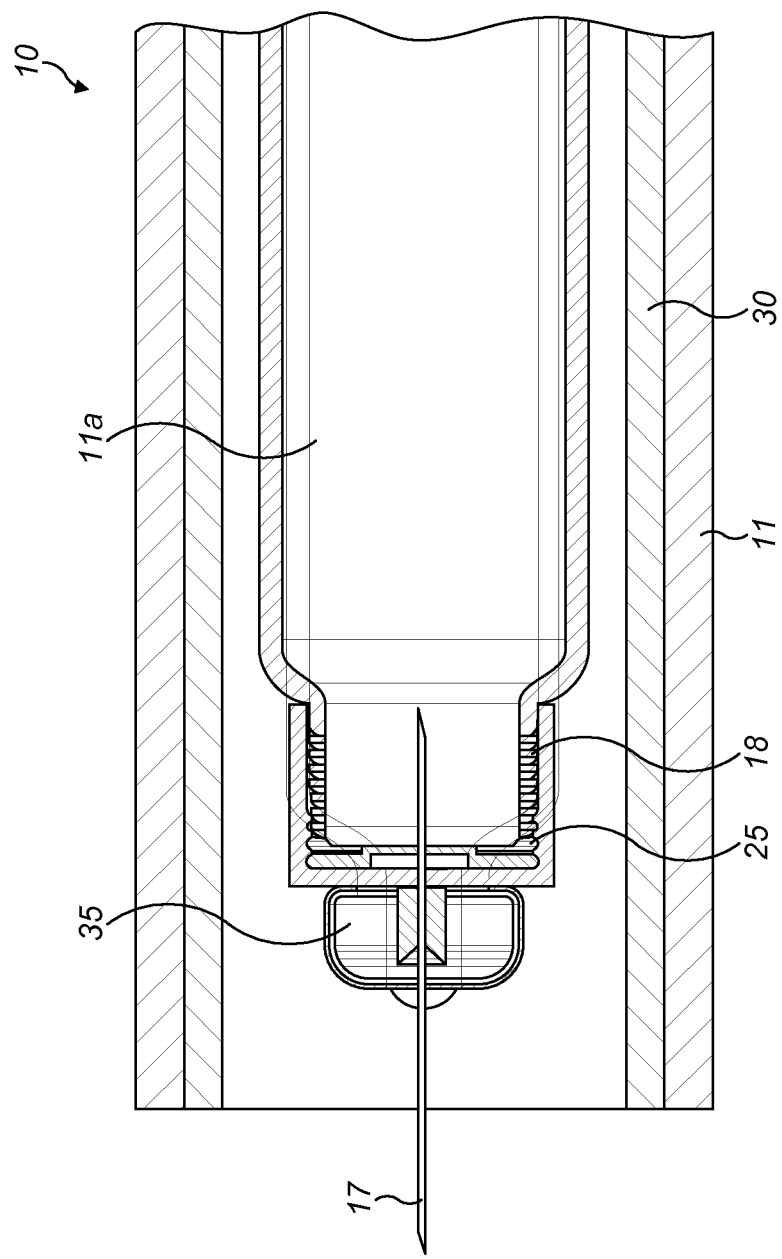
FIG. 5 is a cross-sectional view of the injector device of FIGS. 2, 3, and 4 in a fourth state.
Figure 6:
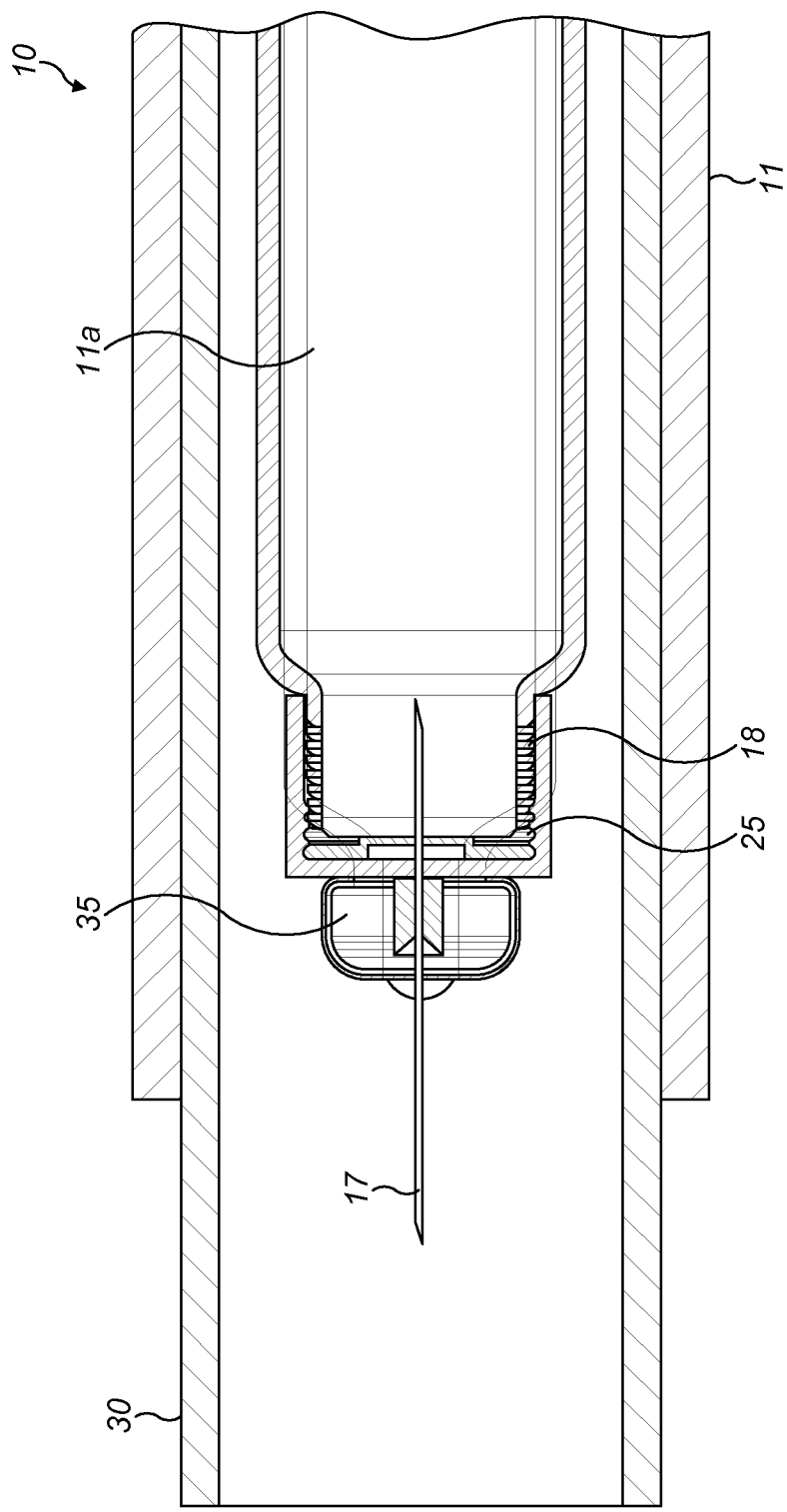
FIG. 6 is a cross-sectional view of the injector device of FIGS. 2, 3, 4, and 5 in a fifth state.

FIG. 4 is a cross-sectional view of the injector device of FIGS. 2 and 3 in a third state, FIG. 5 is a cross-sectional view of the injector device of FIGS. 2, 3, and 4 in a fourth state, and FIG. 6 is a cross-sectional view of the injection device of FIGS. 2, 3, 4, and 5.

After the first fitting mechanism 18 at the cartridge 11a and the second fitting mechanism 24 at the needle assembly 24 are joined together and the hollow injection needle 18 engages with the needle holder 35, the distal end 26 of the removable cap 12 is disengaged from the opening 19 of the housing 11. The retractable sleeve 30 in the third state protrudes from the opening 19 of the housing 11 in order to cover the needle before the injection, as shown in FIG. 4.

As described above, the needle shield 28 is fixedly attached to the removable cap 12 such that it is removable together with the removable cap 12 once the needle assembly 24 is connected to the cartridge 11a via the first and second fitting mechanisms 18, 25. Also, the elastic clip element (not shown in the drawings) releases as the distal end of the removable cap 12 is disengaged from the opening 19 of the housing 11, such that the needle assembly 24 can be detached from the removable cap 12 once it is connected to the cartridge 11a.

Once the removable cap 12 along with the needle shield 28 have been disengaged from the housing 11 of the injector device 10, the needle 17 is exposed at the opening 19 of the housing 11, as illustrated in FIG. 4. However, the user is required to apply force to the retractable sleeve 30 such that it retracts into the housing 11 so as to fully expose the needle 17 for injection as shown in FIG. 5. This will be described in further detail with respect to FIGS. 7 to 11.

After the injection has been performed, the injector device 10 is removed from the injection site, therefore the retractable sleeve 30 is no longer pushed into the housing 11 towards the distal end of the housing 11. By virtue of the spring force provided by the spring element, the retractable sleeve 30 protrudes outwards from housing 11 towards the proximal end of the housing 11. Once the retractable sleeve 30 reaches a certain predetermined protruded status, it is locked in place such that the retractable sleeve 30 can no longer be pushed back into the housing 11. Hence, needle stick injuries can be prevented after injection. The locking feature of the retractable sleeve 30 will be explained in further detail with respect to FIGS. 7 to 11.

A sequence of operation of the injector device 10 according to the first embodiment is as follows:

In the first state, the proximal end 27 of the removable cap 12 is engaged with the opening 19 of the housing 11 of the injector device 10. A user removes the removable cap 12, thus disengaging the proximal end 27 of the removable cap 12 from the opening 19 of the housing 11. The removable seal 29 is then removed from the distal end of the removable cap 12 so as to expose the second fitting mechanism 25 of the needle assembly 24 of the removable cap 12.

The user then reverses the removable cap 12 so as to engage the distal end 26 of the removable cap 12 with the opening 19 of the housing 11. This corresponds to the second state as described above. As described, since both the distal end 26 and the proximal end 27 of the removable cap 12 has a cylindrical shape with the same diameter as that of the opening 19 of the housing 11 (i.e. the round aperture), each of the distal end 26 and the proximal end 27 are engageable with the opening 19.

As the distal end 26 of the removable cap 12 is engaged with the opening 19, the second fitting mechanism 25 of the needle assembly 24 joins with the first fitting mechanism 18 at the cartridge 11a. In the present embodiment, this is achieved via the threaded surfaces provided at the first and second fitting mechanisms 18, 25, i.e. screw-fit. At the same time, the hollow injection needle 17 pierces through the needle holder 35 provided at the cartridge 11a such that the needle holder 35 operationally positions the injection needle 17 for injection.

The removable cap 12 is then disengaged from the opening 19 of the housing 11 again, and the needle shield 28 is removed together with the removable cap 12 so as to expose the hollow injection needle 17. This corresponds to the third state as described above.

In order to trigger an injection, the injector device 10 is pressed against an injection site, e.g. a patient's skin. A user, e.g. the patient or a caregiver, grabs the injector device 10 with their whole hand and pushes the proximal end of the injection 10 against the injection site.

When pushed against the injection site, the retractable sleeve 30 of the injector device 10 retracts into the housing 11 against the spring force biasing the retractable sleeve 30 towards the proximal end of the housing 11, so as to expose the hollow injection needle 17, ready for injection. After the needle 17 has been inserted into the injection site, a plunger arrangement (not shown in the drawings) is activated to push the liquid medicament contained in the cartridge 11a through the needle 17 into the injection site of the patient.

After the injection has been performed, the injector device 10 is removed from the injection site, therefore the retractable sleeve 30 is no longer pushed into the housing 11 towards the distal end of the housing 11. By virtue of the spring force provided by the spring element, the retractable sleeve 30 protrudes outwards from housing 11 towards the proximal end of the housing 11. Once the retractable sleeve 30 reaches a certain predetermined protruded status, it is locked in place such that the retractable sleeve 30 can no longer be pushed back into the housing 11. Hence, needle stick injuries can be prevented after injection.

Since in the first state the needle 17 is not in contact with the cartridge 11a or the rest of the injector components in the housing 11 of the injector device 10, the problem of internal piercing is prevented.

FIGS. 7 to 11 are schematic views of a guide path and a guide pin arranged at the injector device 10, according to the first embodiment. Specifically, FIGS. 7, 8, 9, 10, and 11 illustrate respectively the first, second, third, fourth, and fifth states of the guide pin within the guide path of the injector device 10. The first to fifth states of the guide pin and the guide path correspond to the first to fifth states of the injector device 10 as described above.

Figure 7:
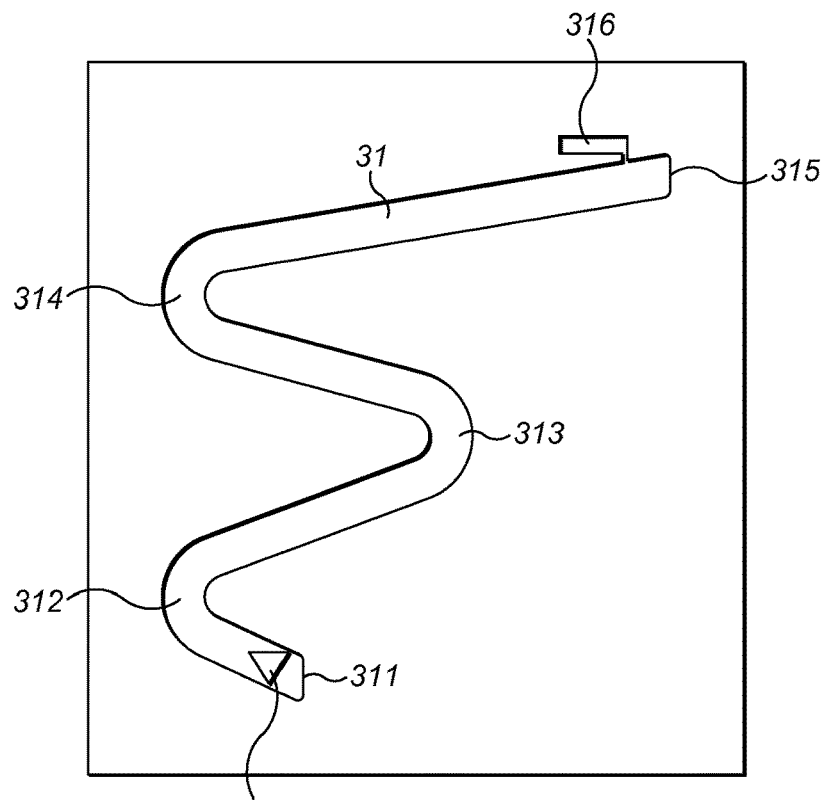
FIG. 7 is a schematic view of a guide path and a guide pin of an injector device according to an embodiment (e.g., the embodiment of FIG. 2) in a first state.

FIG. 7 is a schematic view of a guide path and a guide pin of the injector of FIGS. 2 to 5 in a first state.

In the present embodiment, the retractable sleeve 30 is provided with a guide path 31. The retractable sleeve 30 is a cylindrical sleeve arranged near the proximal end of the injector device 10, and is arranged such that it can protrude from the opening 19 of the housing 11 and be retracted into the housing 11. The retractable sleeve 30 is biased by a spring element (not shown in the drawing) outwards from the opening 19 of the housing 11. The spring element in the present embodiment is a coil spring arranged between the housing 11 of the injector device 10 and the retractable sleeve 30.

Although not shown in the drawings, the retractable sleeve 30 of the present embodiment comprises a first part and a second part. The first part of the retractable sleeve 30 is a distal part of the retractable sleeve 30 that is arranged to come into contact with an injection site when a user presses the housing 11 against the injection site. The second part of the retractable sleeve 30 is a proximal part of the retractable sleeve 30 that is arranged to move axially together with the first part of the retractable sleeve 30 as the retractable sleeve 30, as a whole, is pushed into the housing 11. The second part of the retractable sleeve 30 is further arranged to rotate with respect to the first part of the retractable sleeve 30 as well as the housing 11. Hence, the second part of the retractable sleeve 30 may rotate with respect to the housing 11 while the first part of the retractable sleeve 30 remains stationary and in contact with the injection site. The movement of the retractable sleeve 30 with respect to the housing 11 will be explained in further detail in the following.

The guide path 31 is a groove that is provided at the retractable sleeve 30. In particular, the guide path 31 is provided at the second part of the retractable sleeve 30 in the present embodiment. As illustrated in FIG. 6, the guide path 31 is has a zigzag shape and comprises a first end portion 311, a first bend 312, a second bend 313, a third bend 314, a second end portion 315, and an elastic arm 316. The elastic arm 316 is arranged at the second end portion of the 315 of the guide path 31. The elastic arm 316 is arranged to lock the guide pin 32 in place when the guide pin 32 reaches the second end portion 315 in the guide path 31. This will be explained in more detail with respect to FIG. 11.

The housing 11 of the injector device 10 further comprises a guide pin 32. The guide pin 32 is a protrusion arranged at an inner surface of the housing 11. The guide pin 32 is engaged with the guide path 31 in a way that it is movable along the guide path 31. Specifically, the guide pin 32 can be moved along the guide path 31 by a pushing force exerted by applying force on the retractable sleeve 30 when the user pushes the retractable sleeve 30 against the skin of a patient. In other words, the guide pin 32 can be moved along the guide path through an axial movement of the first part and the second part of the retractable sleeve 30 as well as a rotational movement of the second part of the retractable sleeve 30 with respect to the first part of the retractable sleeve 30 and the housing 11. In the present embodiment, the guide pin 32 has a triangular-shaped cross-section. This triangular shape helps ensure that the guide pin 32 only moves towards the second end portion 315 of the guide path 31, rather than towards the first end portion 311 of the guide path 31.

In the first state, as illustrated in FIG. 7, the guide pin 32 is positioned at the first end portion 311 of the guide path 31. The first state corresponds to the initial state of the injector device 10 as described above, i.e. when the proximal end 27 of the removable cap 12 being engaged with the opening 19 of the housing 11. In this state, the retractable sleeve 30 is kept in a retracted status against the spring force exerted on the retractable sleeve 30 (e.g., because the removable cap 12 is engaged with the opening 19 of the housing 11 as shown in FIG. 2).

Figure 8:
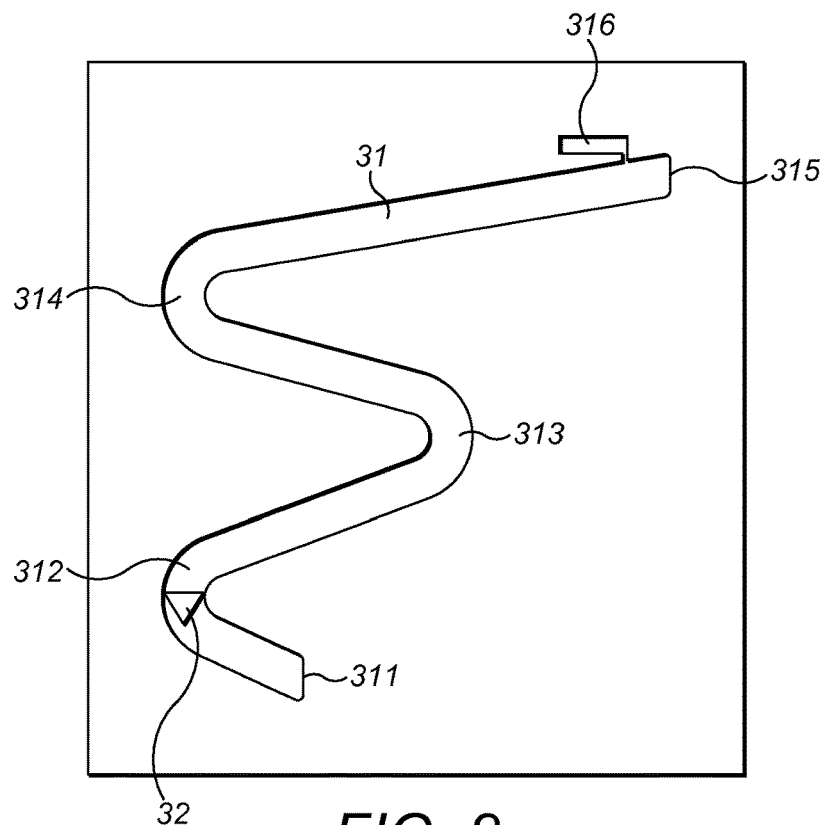
FIG. 8 is a schematic view of a guide path and a guide pin of FIG. 6 in a second state.

FIG. 8 is a schematic view of the guide path and the guide pin of the injector of FIGS. 2 to 5 in a second state.

In the second state, the guide pin 32 arranged on the inner surface of the housing 11 is moved from the first end portion 311 to the first bend 312 in the guide path 31. The second state of the guide path 31 and the guide pin 32 corresponds to the second state of the injector device 10 as illustrated in FIG. 3, i.e. when removable cap 12 is disengaged and then reversed and the distal end 26 of the removable cap 12 is engaged with the opening 19 of the housing 11.

When the distal end 26 of the removable cap 12 is engaged with the opening 19 of the housing, the pushing force of engaging the removable cap 12 with the housing 11 causes the retractable sleeve 30 to retract into the housing 11. Thus, the guide pin 32 to moves from the first end portion 311 to the first bend 312.

The guide pin 32 is prevented from moving further once it has reached the first bend 312, even though the spring force exerted by the spring element biases the retractable sleeve 30 to protrude from the opening 19 of the housing 11. This is because the removable cap 12 is engaged with the opening 19 of the housing 11 which stops the retractable sleeve 30 from extending further.

Figure 9:
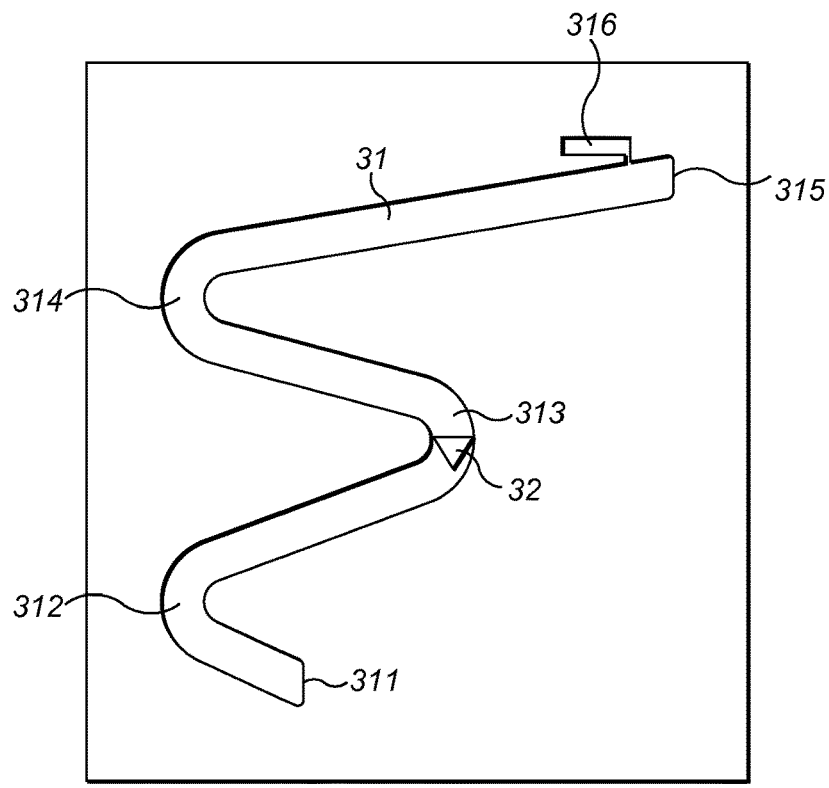
FIG. 9 is a schematic view of a guide path and a guide pin of FIG. 6 in a third state.

FIG. 9 is a schematic view of the guide path and the guide pin of the injector of FIGS. 2 to 5 in a third state.

In the third state, the guide pin 32 arranged on the inner surface of the housing 11 is moved from the first bend 312 to the second bend 313 in the guide path 31. The third state corresponds to the third state of the injector device 10 as illustrated in FIG. 4, i.e. when the distal end 26 of the removable cap 12 is disengaged from the opening 19 of the housing 11.

When the distal end 26 of the removable cap 12 is disengaged from the opening 19 of the housing 11, the spring force exerted by the spring element causes the retractable sleeve 30 to extend further from the opening 19 of the housing 11. This causes the guide pin 32 to move along the guide path 31 from the first bend 312 to the second bend 313. The retractable sleeve 30 in this state serves to shield the needle 17 before injection, so that stick injuries can be prevented.

Since the guide path 31 is in a zigzag shape as shown in FIG. 9, and the guide pin 32 in the present embodiment has a triangular cross-section, the guide pin 32 is arranged to move along the guide path towards the third bend 314 if a force is applied at the retractable sleeve 30 in the longitudinal direction (e.g. when the retractable sleeve 30 is placed on the skin of the patient and the user pushes the injector device 10 towards the skin).

Figure 10:
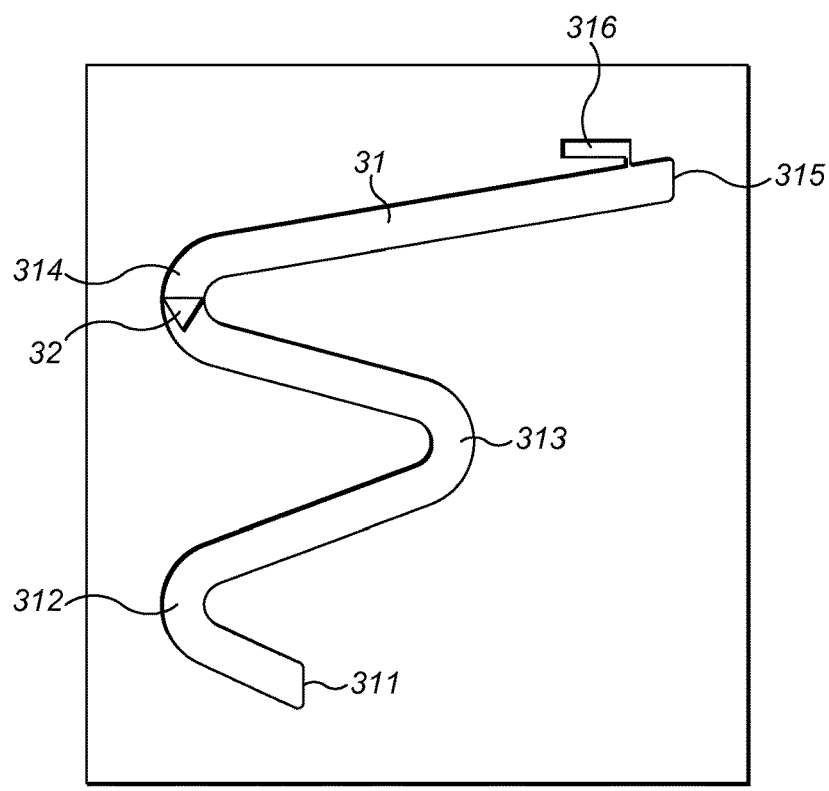
FIG. 10 is a schematic view of a guide path and a guide pin of FIG. 6 in a fourth state.

FIG. 10 is a schematic view of the guide path and the guide pin of the injector of FIGS. 2 to 5 in a fourth state.

In the fourth state, the guide pin 32 arranged on the inner surface of the housing 11 is moved from the second bend 313 to the third bend 314. The fourth state corresponds to the fourth state of the injector device 10 as illustrated in FIG. 5, i.e. when the removable sleeve 30 is fully retracted into the housing 11 of the injector device 10.

Once the guide pin 32 has reached the third bend 314 in the guide path 31, and the retractable sleeve 30 is fully retracted into the housing 11, an automatic trigger (not shown in the drawing) is set off so as to initiate the injection of the medicament contained in the cartridge 11a. Specifically, a plunger arrangement (not shown in the drawings) is activated to push the liquid medicament contained in the cartridge 11a through the needle 17 into the injection site of the patient.

Figure 11:
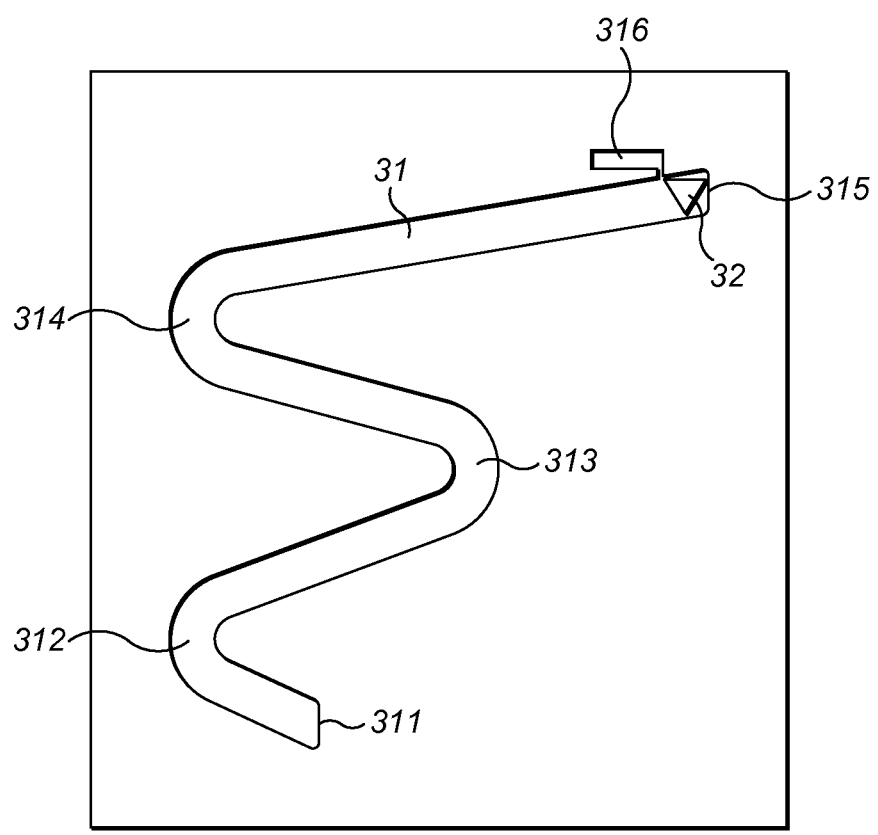
FIG. 11 is a schematic view of a guide path and a guide pin of FIG. 6 in a fifth state.

FIG. 11 is a schematic view of the guide path and the guide pin of the injector of FIGS. 2 to 5 in a fifth state.

After injection, the retractable sleeve 30 is removed from the skin of the patient and therefore the spring force exerted by the spring element causes the retractable sleeve 30 extend outwards from the opening 19 of the housing 11. The guide pin 32 therefore moves from the third bend 314 towards the second end portion 315 in the guide path 31 in the fifth state.

As described above, the elastic arm 316 is arranged at the second end portion 315 of the guide path 31. The elastic arm 316 is arranged to lock the guide pin 32 in place when the guide pin 32 reaches the second end portion 315 in the guide path 31. Since the guide pin 32 is locked in place at the second end portion 315 in this state, the retractable sleeve 30 is locked in place in the extended status and cannot be retracted into the housing 11 anymore. Therefore, the needle 17 is shielded by the retractable sleeve 30 after injection so as to prevent any stick injury.

Although in the above embodiments the injector device 10 is an auto-injector device, in alternative embodiments the injector device 10 may be a manual device in which injection is manually driven.

In alternative embodiments, instead of a screw-fit arrangement, the first fitting mechanism and the second fitting mechanism may form a snap-fit arrangement.

In alternative embodiments, the physical configuration and/or dimensions of the opening of the housing and both ends of the removable cap may be different from what is described above. For example, the removable cap may be configured such that the distal end and the proximal end each comprise a rim having an inner diameter that is the same as a diameter of the opening of the housing, such that opening of the housing can be accommodated into the distal end and the proximal end of the removable cap alternatively. Other configurations may be adopted depending on material costs and other design and/or feature requirements.

In alternative embodiments, the injector device may adopt a standard retractable sleeve for shielding the needle. These standard retractable sleeves do not comprise a guide path, and the housing of the injector device does not comprise a guide pin.

In alternative embodiments, instead of being arranged at the retractable sleeve, the guide path may be provided at the inner surface of the housing of the injector device. In such embodiments, the guide pin is arranged at the retractable sleeve instead of on the inner surface of the housing.

In alternative embodiments, the injector device may not comprise an automatic trigger at the third bend the guide path. The injector device may comprise an actuation element arranged to allow the user to initiate an injection of the medicament. In such embodiments, the user has to manually actuate the actuation element when the retractable sleeve has been fully retracted into the housing of the injector device.

In alternative embodiments, the needle assembly may be supported on the removable cap by other releasable attaching means instead of using an elastic clip element.

In alternative embodiments, the guide path may not comprise the elastic arm. In these alternative embodiments, the guide path may comprise a recess positioned proximate to the second end portion of the guide path such that when the guide pin reaches the second end portion, the guide pin becomes lodged within the recess and becomes locked in place in the recess by virtue of either a shape and/or angle of the recess, or a spring force provided by an additional elastic element that biases the guide pin in place in the recess (e.g. a rotational biasing spring force). In these alternative embodiments, if a rotational biasing spring force is provided, the guide pin may adopt another shape instead of having a triangular cross-section.

In alternative embodiments, the guide path may adopt a shape different from that described above and shown in FIGS. 7 to 11. For example, the guide path may comprise fewer or more bend portions than illustrated in the drawings. For example, the bend portion(s) of the guide path may be designed to have a smaller angle (i.e. a sharper bend). In some alternative embodiments, a combination of a sharper (more angled) bend portion and the use of a guide pin having a triangular cross-section shape may further help ensure that the guide pin only travels in a desired direction. Moreover, in some alternative embodiments, additional elastic arms may be implemented, especially at the bend portion(s), so as to help ensure that the guide pin does not travel in the wrong direction.

In alternative embodiments, the guide pin may adopt another shape instead of having a triangular cross-section.

In alternative embodiments, the elastic arm of the guide path may adopt a different shape or configuration. For example, the elastic arm may be arranged to be bent towards the guide path such that the guide pin may push against the elastic arm as it reaches the second end portion of the guide path. In these alternative embodiments, since the elastic arm is bent towards the guide path, once the guide pin reaches the second end portion it is locked in place by the elastic arm and can no longer travel to other portions of the guide path.

Although it is described above that the opening of the housing has a round aperture defined by the cylindrical wall of the housing having a diameter same as a diameter of the distal end and the proximal end of the removable cap, it will be appreciated that other sizes and configurations of the opening of the housing and the removable cap may be adopted so as to achieve the same effect of a reversibly fitted removable cap with the housing.

In alternative embodiments, the cartridge contained in the housing may not be arranged to be slidable or translatable within the housing. In these alternative embodiments, the cartridge may be arranged within the housing such that the first fitting mechanism is ready to engage with the second fitting mechanism at the removable cap without the need to slide or translate it within the housing before such engagement operation.

In alternative embodiments, the retractable sleeve may not comprise a first part and a second part as described above. In these alternative embodiments, the retractable sleeve may be formed as a single integral component and the guide path may be arranged at an appropriate position at the retractable sleeve. In these alternative embodiments, the guide pin may be moved along the guide path by a pushing force exerted by applying force on the retractable sleeve when the user pushes the retractable sleeve against the skin of a patient, as well as rotating the housing with respect to the retractable sleeve.

Although it is described in the above that the removable seal is made of plastic film or a film of plastic and metal, in alternative embodiments the removable seal may be made of any other suitable materials that fit the requirements of the particular injector and/or liquid medicament. Although claims have been formulated in this application to particular combinations of features, it should be understood that the scope of the disclosure also includes any novel features or any novel combinations of features disclosed herein either explicitly or implicitly or any generalization thereof, whether or not it relates to the same invention as presently claimed in any claim and whether or not it mitigates any or all of the same technical problems as does the present invention. The applicant hereby gives notice that new claims may be formulated to such features and/or combinations of features during the prosecution of the present application or of any further application derived therefrom.

Although a few embodiments have been shown and described, it would be appreciated by those skilled in the art that changes may be made in these embodiments without departing from the full scope and spirit of the invention, the scope of which is defined in the claims.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides.

Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. An injector for delivering a liquid medicament, comprising:
   a housing having an opening at a first end and a cartridge contained within the housing, wherein the cartridge comprises a first fitting mechanism that is directed outwards from the opening of the housing;
   a removable cap comprising a distal end and a proximal end; and
   a needle assembly supported on the removable cap, wherein the needle assembly has a second fitting mechanism, the removable cap being configured such that each of the distal end and the proximal end of the removable cap can be alternatively accommodated into the opening of the housing,
   wherein the first fitting mechanism is complementary with the second fitting mechanism such that the needle assembly is connectable to the cartridge by joining the first fitting mechanism and the second fitting mechanism.

2. The injector of claim 1, wherein the first fitting mechanism and the second fitting mechanism form a snap-fit arrangement or a screw-fit arrangement.

3. The injector of claim 1, wherein the distal end and the proximal end of the removable cap are each cylindrical shaped and have a diameter that is the same as a diameter of the opening of the housing, and wherein the distal end and the proximal end of the removable cap can be alternatively accommodated into the opening of the housing.

4. The injector of claim 1, wherein the needle assembly comprises:
   a hollow needle that opens towards the proximal end of the removable cap; and
   a needle shield arranged to cover the hollow needle.

5. The injector of claim 4, wherein the needle shield is fixedly attached to the removable cap such that the needle shield can be removed together with the removable cap once the needle assembly is connected to the cartridge.

6. The injector of claim 4, comprising a needle holder arranged at a first end of the cartridge, wherein when the needle assembly is connected to the cartridge, the hollow needle is arranged to pierce through the needle holder such that the needle holder operationally positions the hollow needle.

7. The injector of claim 1, wherein the cartridge is arranged to be slidable along a length of the housing towards the opening when the removable cap is removed from the injector.

8. The injector of claim 1, comprising:
   a guide pin arranged on an inner surface of the housing; and
   a retractable sleeve arranged at the first end of the housing;
   wherein the retractable sleeve comprises a guide path, and the guide pin is arranged to be moveable along the guide path such that the extension and retraction of the retractable sleeve is controlled.

9. The injector of claim 8, wherein the retractable sleeve comprises a first part and a second part, wherein the first part is arranged to contact an injection site, and the second part is arranged to move axially together with the first part and to rotate with respect to the first part, and wherein the guide path is arranged at the second part of the retractable sleeve.

10. The injector of claim 8, wherein the retractable sleeve is biased by a spring element towards a proximal end of the housing and outwards from the opening of the housing.

11. The injector of claim 8, wherein the guide path comprises a first end portion, a first bend, a second bend, a third bend, and a second end portion, wherein the first end portion, the first bend, the second bend, the third bend, and the second end portion form a zigzag shape.

12. The injector of claim 11, wherein the guide path comprises an elastic arm arranged at the second end portion of the guide path, the elastic arm being arranged to lock the guide pin in place when the guide pin reaches the second end portion in the guide path.

13. The injector of claim 1, wherein the removable cap comprises a removable seal arranged to cover the distal end of the removable cap.

14. The injector of claim 1, wherein the injector contains medicament.

* * * * *

UNITED STATES PATENT AND TRADEMARK OFFICE
CERTIFICATE OF CORRECTION

| | | |
|---|---|---|
| PATENT NO. | : 11,103,648 B2 | |
| APPLICATION NO. | : 16/300420 | |
| DATED | : August 31, 2021 | |
| INVENTOR(S) | : Uwe Dasbach | |

It is certified that error appears in the above-identified patent and that said Letters Patent is hereby corrected as shown below:

In the Claims

In Column 18, Lines 33-35, in Claim 3, delete "housing, and wherein the distal end and the proximal end of the removable cap can be alternatively accommodated into the opening of the housing." and insert -- housing. --

Signed and Sealed this
Thirty-first Day of May, 2022

Katherine Kelly Vidal
Director of the United States Patent and Trademark Office